United States Patent [19]

Paau et al.

[11] Patent Number: 5,041,383
[45] Date of Patent: Aug. 20, 1991

[54] RHIZOBIUM INOCULANTS

[75] Inventors: Alan Paau, Middleton; Winston J. Brill, Madison, both of Wis.

[73] Assignee: W. R. Grace & Co. - Conn., Columbia, Md.

[21] Appl. No.: 245,927

[22] Filed: Sep. 14, 1988

Related U.S. Application Data

[63] Continuation-in-part of Ser. No. 856,860, Apr. 21, 1986, abandoned, which is a continuation-in-part of Ser. No. 770,727, Aug. 21, 1985, abandoned.

[51] Int. Cl.$^5$ .................. C12R 1/41; C12N 15/00; C12N 1/00; A01C 1/06; C05F 11/08
[52] U.S. Cl. ................ 435/252.2; 435/252.3; 435/172.1; 435/878; 47/57.6; 47/DIG. 9; 71/7
[58] Field of Search ............ 435/34, 878, 172.1, 435/252.2, 252.3; 47/57.6, 58, DIG.9; 71/7

[56] References Cited

U.S. PATENT DOCUMENTS 569,793 .1/1984 Brill et al. ..................... 435/253

OTHER PUBLICATIONS

Kvien et al., 1981, "Recovery of Introduced Rhizobium . . . ", Agron J. 65:916–918.
Maier et al., 1978, "Mutant Strains of Rhizobium japonicum . . . ", Science 201:448–450.
Marking, 1982, Do Your Beans Need Inoculation?, Soybean Digest May/Jun.:28–30.
Noel et al., 1980, Diversity and Dynamics of Indigenous . . . , Appl. & Env. Microbiol. 40(5):931–938.
Handelsman et al., Rhizobium meliloti Competitiveness and . . . , J. Bacteriol. 157(3):703–707, 1984.
Johnson et al., 1965, Competition for Nodule Sites Between . . . , Agron. J. 57:179–183.
Kanicker et al., 1986, Identification of Rhizobium japonicum Nodule Isolates . . . , Appl. & Env. Microbiology 51:487–492.
Kapusta et al., 1973, Influence of Inoculum Size on . . . , Agron. J. 65:916–918.
Dazzo et al., 1975, N.S.F. Annual Report.
Dazzo et al., 1975, Abstract, SEB-ASM Nov. 21-22.
Ham et al., 1971, Agron. J. 63:69–71.
Cho et al., 1985, Kor. J. Appl. Microbiol. Bioeng. 13(1): 79–85.
Van Rensburg et al., 1982, Competitive Abilities of Rhizobium . . . , Appl. Environ. Microbiol. 44(1):98–106.
Roberts et al., 1980, Use of Two-Dimension Polyacrylamide . . . , Appl. & Env. Microbiol. 39(2):414–422.
Semu et al., 1979, Influence of Soybean Inoculation . . . , Can. J. Microbiol. 25:739–745.
Weaver et al., 1974. Effect of Inoculum Rate on Competitive . . . , Agron. J. 66:233–235.

Primary Examiner—Howard J. Locker
Assistant Examiner—David T. Fox
Attorney, Agent, or Firm—Quarles & Brady

[57] ABSTRACT

A method is disclosed for producing novel strains of Rhizobium bacteria for legume inoculants which are both competitive and have high nitrogen fixation characteristics. The method involves first isolating and identifying the naturally predominant strains of the Rhizobium species of interest in a particular locale and then mutagenizing that strain to produce mutant strains which retain the competitiveness and add enhanced nitrogen fixation capabilities.

3 Claims, 3 Drawing Sheets

RHIZOBIUM INOCULANTS

This application is a continuation-in-part of application Ser. No. 06/856,860, filed 4/21/86, now abandoned, which is a continuation-in-part of application Ser. No. 770,727, filed Aug. 21, 1985, now abandoned.

FIELD OF THE INVENTION

The present invention relates to inoculants for leguminous crops in general, and relates, in particular, to a method for creating novel Rhizobium strains which are both biologically competitive and which have high nitrogen fixation ability, and to methods for creating these strains.

BACKGROUND OF THE INVENTION

The phenomenon of the symbiotic relationship between legumes and the Rhizobium bacteria which nodulate their roots is widely known. The bacteria, living in the nodules in the legume roots, fix nitrogen directly from the atmospheric nitrogen thereby converting nitrogen to biologically useful nitrogenous compounds. This process not only provides nitrogen to the plant for protein synthesis, but also enriches the soil in which the legume is grown by leaving nitrogenous nutrients in the soil for later crops. Examples of legumes which are capable of symbiotic relationship with Rhizobium bacteria are peas, beans, alfalfa, red clover, white clover, vetch, and lupines.

Since other agriculturally important plants are unable, either directly or indirectly, to fix nitrogen directly from the air, and thus generally are dependent upon nitrogenous fertilizers to introduce sufficient nitrogen content in the soil for good yield, it is quite common for legumes to be alternated each growing season with non-legume crops in important agricultural areas to facilitate economical enhancement of nitrogen content in the soil. This practice, known as crop rotation, is wide spread Furthermore, some legumes, and in particular soybeans, peas, beans, and alfalfa, are important commercial crops in their own right and growth of these crop plants is greatly facilitated by an ample supply of combined or fixed nitrogen.

There are a number of species of Rhizobium bacteria and different Rhizobium species are adapted to form symbiotic relationships, and nodules, only in the roots of specific legumes. For example, *R. japonicum* nodulates the roots of soybeans, *R. trifolii* nodulates the roots of clovers, *R. meliloti* grows symbiotically with alfalfa and sweet clovers, *R. leguminosarum* is used with peas and vetches, and *R. phaseoli* nodulates the roots of common garden beans. Therefore, in commercial agricultural practices, it is quite a common practice to inoculate the soil or the seeds of the legumes with a culture of the appropriate Rhizobium species. This inoculant is commonly done by coating the seeds before planting, dusting planted seeds, or by spreading the inoculant in the furrows of the planted legume seeds.

In creating and formulating a Rhizobium inoculant, it is desirable that the Rhizobium strain contained in the inoculant have an enhanced ability to fix nitrogen for the benefit of the plant and for soil conditioning. Therefore, much research has logically been conducted on methods for improving the nitrogen fixation of Rhizobium species. Most of the currently commercially available Rhizobium inoculants include strains having high nitrogen fixing ability selected from natural populations.

However, the ability to fix nitrogen does not ensure the survivability of the bacteria in field conditions. Because legumes have been cultivated for many generations in most of the important agricultural areas of the world, many strains of Rhizobium bacteria now freely live indigenously in important agricultural areas. The bacteria may not have been naturally indigenous to all these areas, but introduced strains have populated many of these areas and since they survive freely they may be considered effectively indigenous.

All free-living bacteria, in the soil or elsewhere, are continually subject to environmental pressures, and naturally tend to mutate and be selected by the pressures of the ecological niche which they occupy to be further adapted and competitive for that niche. The indigenous Rhizobium strains are, of course, subject to these pressures. Therefore many of the soils in agricultural areas now contain indigenous Rhizobium strains which have evolved to be adapted for survival in competitive existence in that particular soil environment. Accordingly, even if a farmer introduces into a field a Rhizobium inoculant strain having high nitrogen fixing capability, there is no guarantee that the introduced Rhizobium strain will predominate the roots of the legume plants. The introduced inoculant strain promptly enters into ecological competition with the indigenous strains already present in the soil to nodulate the plants, and, many times, the indigenous populations are an advantage because they are previously selected by ecological pressures for competition in precisely the environment of that field or climatic area. Accordingly, even a high nitrogen fixing Rhizobium strain which can effectively nodulate the legume and fix nitrogen effectively without competition may be an ineffective inoculant in the field since the introduced strain may not actually populate the roots of the legumes, but may be overwhelmed by a locally indigenous strain, which may not have optimal nitrogen fixation abilities. No prior teachings are known on either the desirability of or the process for creating novel Rhizobium strains which are both competitive in field conditions and have high nitrogen fixation abilities.

It has been known previously that legume root exudate can be used to cause Rhizobium cells to develop more lectin-binding sites. It is also known that such exudates can be used as a pretreatment to foster and to enhance the ability of Rhizobium to nodulate when inoculated onto a legume plant.

SUMMARY OF THE INVENTION

The present invention is summarized in that novel strains of Rhizobium bacteria useful as a crop inoculant for legume species in a selected geographic area are created by the method of: isolating a number of Rhizobium cultures from the geographic area; identifying the naturally predominant Rhizobium strain in the geographic area by comparative analysis of the cultures; exposing a culture of the naturally predominant strain to a mutagenic agent; and selecting among the mutagenized bateria for mutants having high nitrogen fixation ability in association with the legumes.

The present invention is also directed toward the novel strains created through the use of this process.

It is an object of the present invention to provide a method for creating novel Rhizobium strains which are both highly naturally competitive for a selected geographic region and also have enhanced nitrogen fixation abilities.

It is another object of the present invention to provide strains selected by this method which are more predictably able to enhance the growth of legume crop plants than presently available Rhizobium inoculant strains.

It is a feature of the present invention in that it is able to select for strain competitiveness and prevalence in particular agricultural environmental conditions without the necessity for simulating the competitive conditions on a bacterial strain in an artifically controlled environment, a simulation which has proven extraordinarily difficult to perfect in practice.

Other objects, advantages, and features of the present invention will become apparent from the following detailed description.

DETAILED DESCRIPTION OF THE INVENTION

Figure 1:
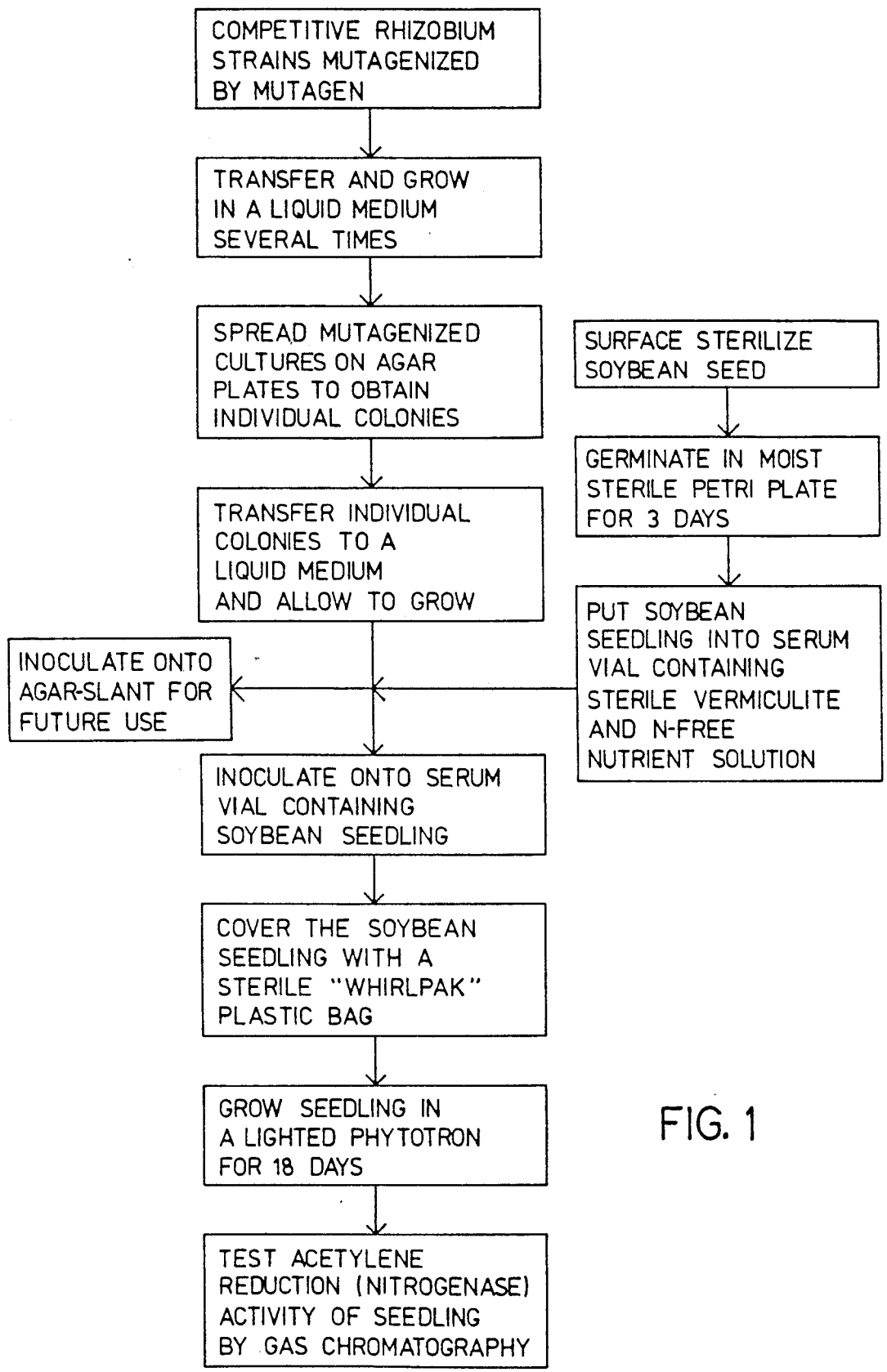
FIG. 1 is a flow chart of the methodology used to generate high nitrogen fixing strains of the competitive Rhizobium strains isolated and identified in accordance with the procedure of the present invention.

The practice of the process of creating novel Rhizobium strains pursuant to the present invention proceeds through a series of steps. First, it is necessary to isolate a number of Rhizobium cultures from a selected geographic area which are then analyzed to identify naturally predominant strains of Rhizobium. The identified naturally predominant strains are then subject to mutagenesis with the mutagenized colonies being selected for high nitrogen fixation. After high nitrogen fixing mutants are discovered, the mutants are returned to field test trial to determine that they both remain competitive and remain sufficiently high nitrogen fixing in the field to increase yield. To fully understand the details of each of these procedures, they will each be discussed in order.

The process of isolation of indigenous Rhizobium cultures to begin with the identification of competitive strains. Contrary to prior strategies for creating Rhizobium inoculants, no effort is taken in accordance with the present invention to try to select for, or engineer for, competitiveness in actual field condition. Instead, the first step is directed toward identifying those indigenous naturally predominant strains which are already present in the selected geographic growing area for the legume crop selected. For example, selecting soybean as a legume, one would select the locales in which soybeans are grown, and identify the strains of indigenous *Rhizobium japonicum* naturally predominant in that locale. As used herein, the term "indigenous" does not mean naturally occurring before the advent of mankind, since *R. japonicum*, for example, is an introduced species in the Western Hemisphere, but refers to the strains which naturally thrive in the soils in the agricultural areas at present. Most soils, for example, in soybean producing areas of the United States now have indigenous local strains of *R. japonicum* naturally present and the strains have evolved to the soil types and climatic regions of the country.

The determination and identification of the competitive strains proceeds first by the large scale collection of nodules from the legume cultivation region which has been selected. Legume crop fields are located which have not been inoculated with any Rhizobium inoculant. Plants are removed from the fields, and the nodules are harvested from the roots of plants grown in those fields. The nodules are surface-sterilized and then crushed so that the Rhizobium colonies therein can be accessed. Cells from the crushed nodules are plated onto suitable growth media, i.e. nutrient agar medium, and are cultivated in the laboratory. These strains can then proceed through the strain identification process.

Identification of bacterial strains is an evolving technology at present. At present, most strains of bacteria are identified and classified based on the results of a series of tests. The tests include examinations of morphology, bacterial serology, quantitative antibiotic sensitivity of the various strains, phage sensitivity of the strains, and the protein pattern created by a strain by one or two dimensional polyacrylamide gel electrophoresis. Any or all of these techniques may be used together to identify the strains. The most advantageous technique used by the applicants here, and considered the best combination of ease and effectiveness, is one-dimensional gel electrophoresis.

Perferably, large numbers of nodules are collected and large numbers of Rhizobium cultures are obtained from the particular locale for the crop in question. For example, it is appropriate to obtain cultures for hundreds, if not thousands, of Rhizobium strains from a given geographic area, and a given crop such as soybean. These thousands of strains are then analyzed by gel electrophoresis. The electrophoresis gel patterns are then analyzed. Those patterns which predominate in the growing areas are defined, for purposes of this procedure, to characterized the strains which are naturally predominant. In other words, the large numbers of gel plates are analyzed and placed into groups reflecting the groupings of the gel patterns. The numbers of cultures falling in each group are then compared to determine which of the groupings, or strains, is most represented and therefore predominates in the particular region under consideration. Those isolates which are found to have identical gel patterns are defined to be the same strain. It will be discovered that different frequently isolated strains will be found to be differentially competitive in different growing regions, and that certain strains will seem to predominate in any one localized growing region.

It has been found that geographical regions which cover multi-state regions may be determined to have sufficiently common agricultural, environmental and climactic conditions that a single strain, at at most a very small number of strains (two or three), are predominant in such a region. The geographic size of such a region can be quite large as long as the same indigenous strain or strains are predominant throughout the region. The proper size for such a region may be determined by the extent to which a single, or at most a very few, strains are predominant over the region. To be predominant over the region, the strain need not be dominant in every field in every locale in the region, but must be sufficiently predominant that a statistical sample of fields in the region will yield the predominant strain more than any other.

For example, it has been found that the legume growing region of the Missippi delta region of the U.S. is a good example of such a multi-state region. This concentrated soybean-growing area including the areas of southeastern Missouri, western Tennessee, western Mississippi, eastern Arkansas, and Louisiana was found to have two strains which together were naturally predominant throughout the region.

Once the most widely isolated strain in a given growing region is determined, that strain is considered the naturally predominant and competitive strain for purposes of this procedure. In order to fully verify its competitiveness, and to ensure that the strain has not previously mutated while in culture, it is then appropriate to conduct a field test of the strain to ensure that it nodulates properly and that its competitive is replicatable in the actual field environment. Also appropriate is a test for nitrogen fixing activity. This step can be performed in green house or phytotron on individual plantlets in pots or trays. The plants are inoculated with the putative predominant competitive strain and then are assayed for acetylene reduction. This not only verifies that the nitrogen fixing activity of the strarn occurs in conjunction with the selected crop plant, but serves as a base line for later efforts to select for increased nitrogen fixing activity.

The confirmation test for competitiveness is a field test for nodulation activity. This is done by planting fields of the putative naturally predominant competitive strain. Controls should include both uninoculated seeds and plants inoculated with commercial, but presumably less-competitive, strains. In order to be deemed a successful naturally predominant competitive strain, The selected strain should be recoverable from nodules in inoculated plants at a rate significantly higher than recoverable from plants which were either not inoculated or inoculated with non-competitive strains and also at a rate significantly higher than the commercial strain can be recovered from nodules.

Strains which can be re-isolated at high frequency from nodules of legume plants inoculated with the strain of interest are determined for purposes of experiment to be naturally predominant and competitive under field conditions. Thus at this stage of the procedure strains have been isolated and identified which are indigenous, but which can also withstand laboratory isolation and be reintroduced while retaining their competitiveness. In addition, since by this step we have verified that the nodulation of the plants is increased by inoculation of this strain, it is also demonstrated that increased nodulation can be obtained through the use of this strain, even without enhanced nitrogen fixing activity.

The next step is to proceed to mutagenize cultures of the naturally dominant strains. Cultures of the strains are exposed to a mutagenic agent, such as radiation or a chemical agent. It is preferred within the present experiment that the mutagen used is the chemical mutagen nitrosoguanidine. The bacteria exposed to the mutagen are transferred and allowed to grow Out several times in a liquid medium. The mutagenized cultures are then spread on agar plates to obtain individual colonies. Once individual colonies are established, the colonies are again transferred to a liquid medium and allowed to grow out. Samples of each of the grown out colonies can then be inoculated into a serum vial containing a seedling of the legume plant to which the Rhizobium is associated. The seedling is isolated from the environment, such as by covering with a sterile transparent container, and then is grown under conditions fostering the growth of the legume plant. After a period of time, an assay for nitrogen fixing activity, again accomplished by testing for acetylene reduction activity of the seedlings by gas chromatography or other similar process is performed. By comparing the comparative nitrogen fixing activity of the mutated bacteria with the base line for the naturally predominant strain, mutagenized progeny which have enhanced nitrogen fixing activity can be isolated. The strains having the most promising nitrogen fixing activity can then be returned to culture and grown out to provide sufficient quantities for additional field testing. Once high nitrogen fixing candidate mutant strains have been identified, those strains must then be analyzed again to ensure that the natural competitiveness has not been lost through the mutation process. Accordingly, all the candidate strains must again be grown out and must be individually tested for competitiveness in actual field trials. Concurrently, nitrogen fixing trials can be replicated in greenhouse or phytotron to ensure repeatable and reliable enhanced nitrogen fixation capability. Competitiveness can only be truly assessed in field trials because of the state of the art of the technology of replicating competitive field conditions in the greenhouse or phytotron. Thus the strains are then grown ou& and inoculated into the appropriate legume plants in the crop growing areas. Then the populations of the nodules in the plants can be examined midseason to determine which strains of bacteria are populating those nodules. For those strains which remain competitive and achieve enhanced nitrogen fixing activity, those strains should be present in the nodules in numbers quantitatively increased over non-competitive strains. In addition, fields containing the mutant strains having high nitrogen fixation and competitive advantages should give enhanced yield over those fields having no inoculant or other commercial, non-competitive strain, inoculants available.

DETAILED DESCRIPTION OF EXAMPLE

It was decided to generate novel strains of *Rhizobium japonicum* bateria for particular uses as a soybean inoculant in two major soybean-producing areas of the United States. As a first step in this process, an effort was undertaken to identify the naturally predominant strains of *R. japonicum* through the Mississippi delta soybean growing region, including all or part of the states of Missouri, Tennessee, Mississippi, Arkansas, and Louisiana, as well as in parts of soybean growing areas of the midwest such as in the state of Iowa. Louisania. Field teams visted soybean fields in each state in which no commercial inoculant was applied to the fields during planting. Nodules were recovered from soybean plants in the fields. The nodules were surface sterilized and crushed. Rhizobium cells isolated from the nodules were then plated on to a nutrient agar medium, in which they were cultured and returned to the laboratory.

In the laboratory, cultures of the strains were grown up and then analyzed using one-dimensional gel polyacrylamide gel eletrophoresis. Protein gel patterns were created for each of the Rhizobium isolates obtained from each state. The gel patterns from the isolates were then comparatively analyzed to determine which patterns were predominant in each of the two designated states. That analysis was able to identify certain gel patterns which predominated from the samples taken. The gel patterns were grouped and assigned tentative strain numbers, numbers assigned to the groups of gel patterns to help group the patterns into related strains.

From the Iowa samples, the strain designated IA2838 was identified, along with one other Iowa strain, as the most predominant. From the Louisiana samples, a strain designated LA1304 was determined, again along with one other strain, designated strain LA1325 to be the strains best represented among the gel patterns. For purposes of these procedures, both the strains LA1304 and LA1325 were determined to be naturally predominant strains.

In fact, after isolating thousands of *Rhizobium japonicum* strains from throughout the Mississippi delta region, it was determined that the two strains LA1304 and LA1325 could together be considered naturally predominant throughout the region. The following table illustrates the relative abundance of these strains in these states.

TABLE

|  | 1 | 2 | 3 |
|---|---|---|---|
| Louisiana | LA1325 | LA1304 | X |
| Mississippi | LA1304 | LA1325 | X |
| Arkansas | LA1304 | X | LA1325 |
| Tennessee | X | LA1304 | X |
| Missouri | LA1325 | X | X |

In the table "X" indicates other strains. The strains are ranked by order of relative abundance for each state.

In order to verify the infective activity of these Rhizobium strains, a phytotron test of infectivity of each of these Rhizobium strains was conducted. Bacteria from each strain was inoculated onto soybean seeds grown up individually in the phytotron. Acetylene reduction assays were taken on the young soybean plants to indicate relative nitrogen fixing activity of the strain when inoculated into the soybeans. Both of these strains were found to be infective in soybean and to form nodules in the roots of soybean plants, and to exhibit reasonable, though not enhanced, acetylene reduction activity indicating nitrogen fixation.

To verify that these strains were indeed predominant and competitive in the locales from which they were isolated, a field test was conducted using the naturally predominant strains in actual field conditions. The strains were used as an inoculant during planting under normal local soybean growing practices in soybean fields in both Iowa and Louisiana. To investigate the differential competitiveness on the Iowa and Louisiana strains, naturally competitive strains from both locales were inoculated into fields in both areas. In the field trials in each state, there were double controls, one control being plants which were not inoculated intentionally with any inoculant, and the second control being planted with a commercially available inoculant from Nitragin Co. In the Iowa site, the Iowa naturally predominant strains were identified in 37% of the total Rhizobial population recovered from nodules of uninoculated plants. This indicates a population of this naturally occurring strain sufficient to cause nodulation in plants even without intentional inoculation. Where the commercial inoculant was used, bacteria corresponding to the experimental Iowa naturally predominant strain were found in 30% of the total Rhizobial population in nodules recovered. For the plants in which the experimental inoculant was utilized, 67% of the Rhizobial population in nodules were found to be the Iowa strains of naturally predominant bacteria. By contrast, only 5% of the Rhizobial population in nodules were found to be bacteria corresponding to the Louisiana naturally predominant strains, which were also included in the experimental inoculant. Similar results were obtain in the Louisiana site where the uninoculated plants had nodules which were occupied at 33% by the Louisiana naturally predominant strains, the Nitragin Co. inoculated plants yielded the naturally predominant strains in 13% of the Rhizobial population in their nodules, and the experimentally inoculated plants had the naturally predominant strains in 63% of the Rhizobial population in their nodules. The experimental inoculant again included populations of both naturally predominant strains. At the Iowa site, only about 5% of the Rhizobial population in nodules contained bacteria of the naturally predominant Louisiana strain, with a similar result being reached for the naturally predominant Iowa strains at the Louisiana site. Thus it was determined that the naturally predominant strains effectively nodulated plants in field conditions and were very competitive with existing indigenous Rhizobium and with other inoculants to compete for nodulation sites in soybean roots. In addition, it was also made clear by this test that for each of the two geographic locales selected, the naturally predominant strains from those locales were superior in each locale to the naturally predominant strain from the other.

Once the competitiveness and nodulation activity of the naturally predominant strains was verified, the strains were then mutagenized and selected for high nitrogen fixation activity. Shown at FIG. 1 is a flow chart of the process used to perform this step. The chemical mutagen used was nitrosoguanidine. The bacteria were exposed to the mutagen and then transferred and allowed to grow in a liquid medium several times. The mutagenized colonies were then spread on agar plates to obtain individual colonies which were again transferred to a liquid medium to grow out. Bacteria from the grown out colonies were placed on soybean seedlings grown out from surfaced sterilized soybean seed grown in a moist sterile petri plate for three days. The soybean seedling and the inoculant was placed in a serum vial containing sterile vermiculite and nitrogen free nutrient solution. The soybean seedling was covered with a sterile plastic bag and grown in a lighted phytotron for 18 days, after which the acetylene reduction activity was determined by gas chromatography. Mutagenized colonies which showed the best nitrogen fixing activity (acetylene reduction activity) were reinoculated into additional plants and retested to verify that the activity was replicatable.

Figure 2:
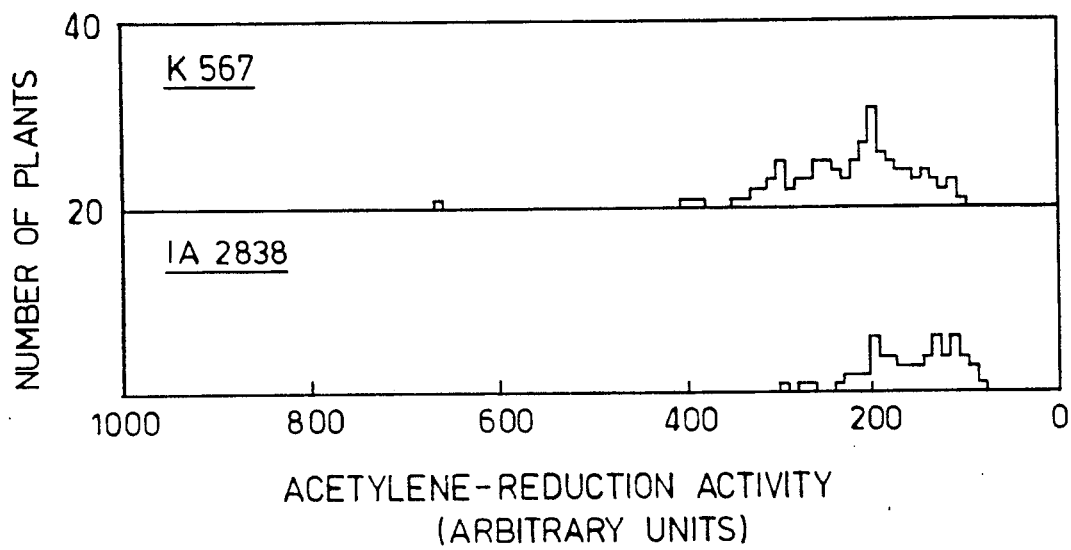
FIG. 2 is a chart illustrating the enhancement of nitrogen fixation activity obtained from one mutagenized naturally predominant strain.
Figure 3:
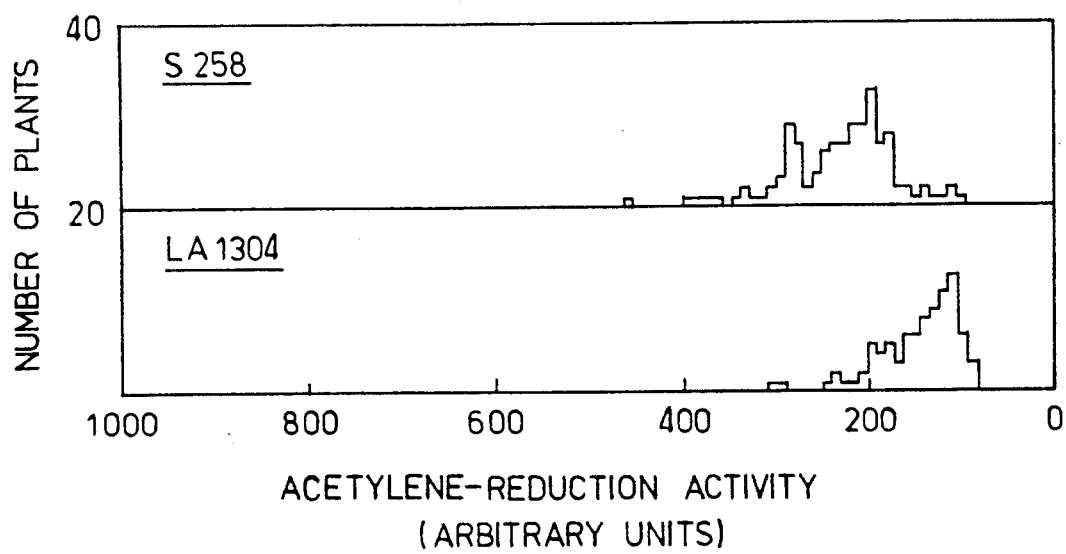
FIG. 3 is a chart of the enhanced nitrogen fixing activity obtained from a second strain.

Shown in FIGS. 2 and 3 are charts illustrating the enhancement of nitrogen fixation activity obtained from the mutagenized strains. Illustrated in FIG. 2 demonstrates the relative acetylene reduction activity of strain LA1304 compared to LA1304 Louisiana-derived strain K567, which a mutagenized version of IA2838. The units are arbitrary. Shown in FIG. 3 is a similar chart showing the enhanced nitrogen fixation activity of strain S258 which is another high-nitrogen fixing mutant of naturally competitive strain Louisiana LA1304.

The mutant strains S258 and K567 were then used as inoculants in actual field tests to attempt to verify competitiveness and increased nitrogen fixation activity by measuring yield. Each strain was tested against its wild type ancestor. Strain S258 inoculated using a peat formulation exhibited a 9.9% increase in yield over its wild type ancestor used similarly as an inoculant in Louisiana on soybean of variety Centennial. On a similar test utilizing a peat formulation grown in Illinois on Williams 82 soybeans, no difference in yield was obtained between the mutant strain and the wild type. Strain K567 inoculated using a peat formulation, as compared to strain LA1304, also inoculated using a peat formulation, on fields of Corsoy 79 and Williams 82 soybeans in fields in Ohio and Wisconsin exhibited an average yield increase of 13.4%. Field trials of both of these strains were conducted using uninoculated fields and also against using an existing commercial inoculant (Nitragin), and both mutated strains showed statistically significant yield enhancement over both these controls also.

Five enhanced nitrgogen-fixing mutants of LA1304 and LA1325 were developed and then combined as a field crop inoculant for soybeans in the Mississippi delta region. The inoculant was sent to state agricultural universities in three states in the region, Louisiana, Missouri, and Tennessee, for field tests to evaluate its efficacy in yield enhancement in soybean fields know to have indigenous *Rhizobium japonicum* populations. The inoculant strains were applied in a vermiculite-based microbiologically-pure formulation as described in Graham-Weiss et al., *Appl. Envir. Microbiol.*, 53, p. 2138 (1987).

The following table summarizes the results of these field tests.

TABLE

|  | Yield change | |
| --- | --- | --- |
|  | Bushel/ave. | % |
| Louisiana | 3.1 | 8.0 |
| Missouri | 1.0 | 2.4 |
| Tennessee | 2.2 | 7.8 |
| Regional | 2.5 | 6.5 |

This indicates that the enhanced nitrogen fixing instant strains retain sufficient competitiveness to be effective to increase yield throughout the legume cultivation region of the Mississippi delta. These results suggest that similar results can be obtained in other regions in which one or two naturally indigenous strains can be found to predominate over the entire region.

It is also possible to further enhance the nodulation competitiveness of these competitive mutant strains. If the speed with which the Rhizobium begin the nodulation process can be increased, the first nodulating bacteria will have a competitive advantage, because they already occupy the nodules, over other strains. It is already known that soybean root extract can be used to enhance the nodulation activity of *Rhizobium japonicum* strains. This phenomenon also is effective with the novel strains produced by the present process.

To verify that effect, soybean seeds were germinated in soil contained in clear plastic containers. The seeds were sprouted and, after sprouting, a mark was made on the container indicating the position of the root tip. The soil was then inoculated with a viable culture of *Rhizobium japonicum* strain K567. The plants were allowed to grow out and then the nodules in the roots of the plants were scored, both for number and for location relative to the root tip marker. Control plants were inoculated with untreated K567 bacteria while experimental plants were inoculated with bacteria pre-treated with a nutrient broth in which soybean seedlings had been previously grown.

Figure 4:
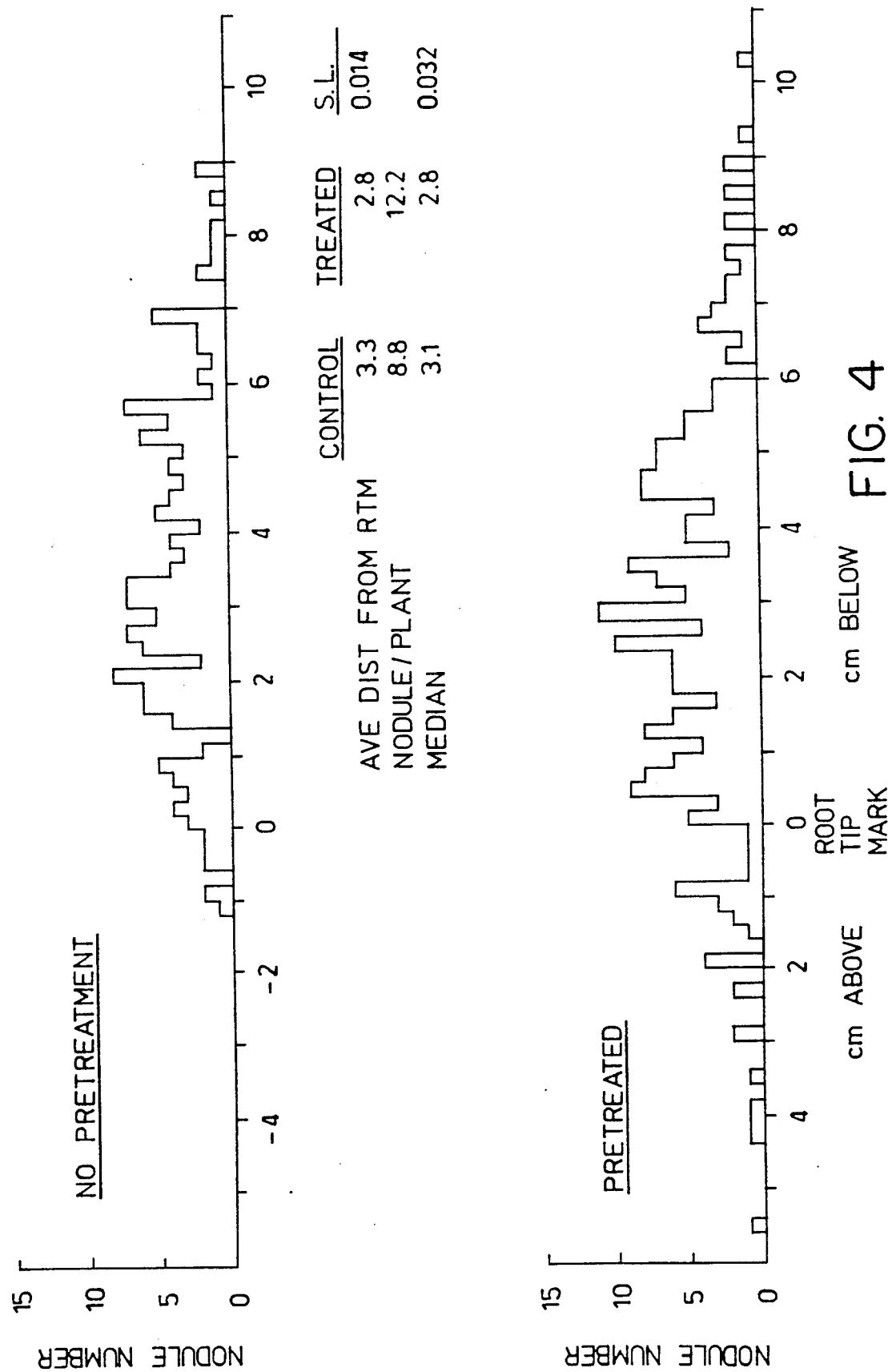
FIG. 4 is a chart illustrating enhancement of nodulation obtained by inoculant pre-treatment.

The results are displayed in FIG. 4 and Table 1 below. FIG. 4 indicates that there were elevated numbers of nodules overall in the experimental plants and that the nodules were generally higher on the plant roots, indicating faster nodule formation. Table 1 verifies this result. Therefore, this pre-treatment phenomenon is effective even for the novel competitive strains created by this process.

TABLE 1

|  | Control | Pre-Treated |
| --- | --- | --- |
| Average distribution of the Uppermost nodule from the root tip marker (rtm) (minus indicates above the r.t.m.) | −0.02 cm | −0.49 cm |
| Percent of nodulation below the r.t.m. | 82.4% | 84.5% |
| Percent of nodulation on lateral roots | 32.0% | 4.9% |
| Nodules per plant on primary root | 1.9 | 8.3 |
| Nodules per plant on lateral root | 2.7 | 1.5 |

Thus this example demonstrates that novel competitive and high nitrogen fixing strains of Rhizobium bacteria can be created using the process of the present invention. This approach has two advantages over approaches previously known in the technology. This approach manages to select competitive Rhizobium bacteria without having to attempt to mimic competitive any field conditions in order to select for strains that would be competitive in the field. Previous inoculant strains have not been properly competitive, and the state of the art in mimicking field conditions to accurately select for competitiveness is not very sophisticated. In addition, this approach does not require that the experimenter identify, quantify, or even study which characteristics of the Rhizobium itself are necessary or advantageous in making the strain competitive in the field (i.e. able to become a major occupant in nodules of soybeans or other legumes grown in field crop conditions). This process takes advantage of the natural adaptation of Rhizobium activity occurring in agricultural fields in any event.

The following microorganisms have been deposited with the American Type Culture Collection, 12301 Parklawn Drive, Rockville, MD, U.S.A. (ATCC) and also with the Cetus Master Culture Collection (CMCC) maintained by Cetus Corporation, Emeryville, CA, with the following accession numbers:

| Culture | CMCC# | ATCC# | ATCC Deposit Date |
| --- | --- | --- | --- |
| LA1304 | 1886 | 53537 | September 10, 1986 |
| IA2838 | 1885 | 53538 | September 10, 1986 |
| S258 | 2847 | 53536 | September 10, 1986 |
| K567 | 2848 | 53535 | September 10, 1986 |

We claim:

1. *Rhizobium japonicum* bacteria of strain K567, ATCC accession No. 53535.

2. *Rhizobium japonicum* bacteria of strain S258, ATCC accession No. 53563.

3. An inoculant for soybean plants comprising a carrier, and *Rhizobium japonicum* bacteria of at least one of the strains No. 53535, and strain S258, ATCC accession No. 53536.

* * * * *

UNITED STATES PATENT AND TRADEMARK OFFICE
CERTIFICATE OF CORRECTION

PATENT NO. : 5,041,383
DATED : August 20, 1991
INVENTOR(S) : Alan Paau and Winston J. Brill It is certified that error appears in the above-identified patent and that said Letters Patent is hereby corrected as shown below:

Column 8, line 60, delete "LA1304" (second occurrence).

Column 8, line 61, delete "IA2838" and insert therefor --LA1034--

Column 9, line 12, delete "Wisconsin" and insert therefor --Illinois--.

Column 9, line 13, delete "13.4%" and insert therefor --9.8%--.

Column 10, In Claim 2, line 2, delete "53563" and insert therefor --53536--.

Column 10, In Claim 3 line 3, between the words "strains" and "no." insert --selected from the group consisting of strain K567, ATCC Accession--.

Signed and Sealed this

Twenty-second Day of November, 1994

Attest:

BRUCE LEHMAN

*Attesting Officer*          *Commissioner of Patents and Trademarks*